(12) United States Patent
Iizuka (10) Patent No.: US 9,955,853 B2
(45) Date of Patent: May 1, 2018

(54) DISTAL END STRUCTURE OF ENDOSCOPE

(71) Applicant: OLYMPUS CORPORATION, Tokyo (JP)

(72) Inventor: Tomoyuki Iizuka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/266,291

(22) Filed: Sep. 15, 2016

(65) Prior Publication Data

US 2017/0000317 A1 Jan. 5, 2017

Related U.S. Application Data

(63) Continuation of application No. PCT/JP2015/060466, filed on Apr. 2, 2015.

(30) Foreign Application Priority Data

Aug. 7, 2014 (JP) .................................. 2014-161447

(51) Int. Cl.
*A61B 1/00* (2006.01)
*A61B 1/018* (2006.01)
(Continued)

(52) U.S. Cl.
CPC ............ *A61B 1/00101* (2013.01); *A61B 1/00* (2013.01); *A61B 1/00091* (2013.01);
(Continued)

(58) Field of Classification Search
CPC .......................... A61B 1/00101; A61B 1/00103
(Continued)

(56) References Cited

U.S. PATENT DOCUMENTS 4,881,810 A * 11/1989 Hasegawa .......... A61B 1/00101
356/241.5
5,104,379 A * 4/1992 Nakamura ......... A61B 1/00062
604/111
(Continued)

FOREIGN PATENT DOCUMENTS

JP 2004-317623 A 11/1992
JP 09-075295 A 3/1997
(Continued)

OTHER PUBLICATIONS

International Search Report dated Jun. 30, 2015 issued in PCT/JP2015/060466.
(Continued)

*Primary Examiner* — Matthew J Kasztejna
(74) *Attorney, Agent, or Firm* — Scully, Scott, Murphy & Presser, P.C.

(57) ABSTRACT

A distal end structure of an endoscope according to the present invention includes a distal end member formed of a metal material, an insulating ring provided in an annular shape around an insertion axis on a proximal end side of the distal end member, a cover formed of a flexible insulative material that covers the distal end member, a projecting section provided integrally with the insulating ring and projecting in a direction crossing the insertion axis, a through-hole provided in the cover and engaging with the projecting section, and a to-be-torn-apart section provided near the through-hole, in which force is applied to the to-be-torn-apart section to tear apart the cover along the insertion axis direction and remove the cover from the distal end member.

12 Claims, 9 Drawing Sheets

(51) Int. Cl.
*A61B 1/06* (2006.01)
*A61B 1/12* (2006.01)
*G02B 23/24* (2006.01)

(52) U.S. Cl.
CPC ...... *A61B 1/00096* (2013.01); *A61B 1/00098* (2013.01); *A61B 1/00135* (2013.01); *A61B 1/00137* (2013.01); *A61B 1/018* (2013.01); *A61B 1/0615* (2013.01); *A61B 1/126* (2013.01); *G02B 23/243* (2013.01)

(58) Field of Classification Search
USPC .................................................. 600/127, 129
See application file for complete search history.

(56) References Cited

U.S. PATENT DOCUMENTS

| | | | | |
|---|---|---|---|---|
| 5,662,588 A | * | 9/1997 | Iida | A61B 1/00091 600/121 |
| 5,674,181 A | * | 10/1997 | Iida | A61B 1/0008 600/121 |
| 5,730,701 A | | 3/1998 | Furukawa et al. | |
| 5,788,628 A | * | 8/1998 | Matsuno | A61B 1/00091 600/121 |
| 5,860,913 A | | 1/1999 | Yamaya et al. | |
| 5,865,726 A | * | 2/1999 | Katsurada | A61B 1/0008 600/121 |
| 6,878,107 B2 | * | 4/2005 | Hino | A61B 1/0008 600/121 |
| 6,916,284 B2 | * | 7/2005 | Moriyama | A61B 1/00089 600/127 |
| 8,038,604 B2 | * | 10/2011 | Hamazaki | A61B 1/0008 600/107 |
| 8,747,304 B2 | * | 6/2014 | Zeiner | A61B 1/00087 600/104 |
| 2017/0000317 A1 | * | 1/2017 | Iizuka | A61B 1/00 |

FOREIGN PATENT DOCUMENTS

| | | |
|---|---|---|
| JP | 09-299316 A | 11/1997 |
| JP | 2002-017654 A | 1/2002 |
| JP | 2003-102668 A | 4/2003 |
| JP | 2003-230531 A | 8/2003 |
| JP | 2007-289434 A | 11/2007 |
| JP | 2009-219572 A | 10/2009 |

OTHER PUBLICATIONS

Japanese Office Action dated Mar. 22, 2016 issued in JP 2015-560436.

* cited by examiner

DISTAL END STRUCTURE OF ENDOSCOPE

CROSS REFERENCE TO RELATED APPLICATION

This application is a continuation application of PCT/JP2015/060466 filed on Apr. 2, 2015 and claims benefit of Japanese Application No. 2014-161447 filed in Japan on Aug. 7, 2014, the entire contents of which are incorporated herein by this reference.

BACKGROUND OF THE INVENTION

1. Field of the Invention

The present invention relates to a distal end structure of an endoscope in which a single use cover is attached to a distal end member provided at an endoscope distal end.

2. Description of the Related Art

There has been known an endoscope in which a high-frequency treatment instrument is used. The endoscope of this type has a structure in which, in order to safely use the high-frequency treatment instrument, a surface of an elongated insertion section is coated with an insulative resin material, an insulative rubber member is further disposed in an exterior portion of a bending section disposed on a distal end side of the insertion section, and a cover formed of an insulative material is attached to a distal end portion to insulate the entire insertion section of the endoscope. By attaching the cover, when an insertion section distal end is inserted into a bent body cavity of a human body or the like, even if the insertion section distal end touches a body cavity inner wall, it is possible to protect the body cavity inner wall from damage.

When safety is taken into account, the cover is desirably fixed to the distal end portion by an adhesive. However, the endoscope needs to be sufficiently cleaned and disinfected after use. For example, when a mechanical component such as a raising base for raising a treatment instrument is housed in the distal end portion, gaps among respective components are narrow and cleaning work takes time.

Therefore, for example, there has been known an endoscope in which a cover is enabled to be attached and detached, in cleaning and disinfection, the cover is detached from a distal end portion to make it easy to clean both of the cover and the distal end portion, and the cover can be attached to the distal end portion after the cleaning.

However, for a reusable cover, complicated work for, for example, pushing in the cover while rotating in reattachment is requested to prevent the cover from coming off or positionally deviating during use. There is also a problem in that material characteristics change because of repeated use of the cover.

As measures against this problem, for example, Japanese Patent Application Laid-Open Publication No. 2007-289434 proposes a technique for attaching a single use cover to a distal end portion. That is, in the cover disclosed in the patent literature, a finger hook section is provided on one side. The finger hook section is pinched and pulled by fingers to tear off a thin portion and a recessed groove formed near the finger hook section to detach the cover from the distal end portion.

The cover disclosed in the patent literature is configured such that a groove section is formed on an inner surface in order to prevent the cover from coming off a distal end portion after attachment, the groove section is engaged with a locking section formed at the distal end portion, and, when the thin portion is torn off from the cover, the groove section and the locking section are disengaged.

SUMMARY OF THE INVENTION

According to an aspect of the present invention, there is provided a distal end structure of an endoscope formed to extend along an insertion axis. The distal end structure of the endoscope includes: a distal end member formed of a metal material; an insulating member provided around the insertion axis on a proximal end side of the distal end member; a cover formed of a flexible insulative material that covers the distal end member; a projecting section provided integrally with the insulating member and projecting in a direction crossing the insertion axis; an opening window provided in the cover to expose a part of the distal end member; a through-hole provided between the opening window in the cover and a proximal end portion of the cover and engaging with the projecting section; and a to-be-torn-apart section provided on both width direction sides of the through-hole in the cover to linearly extend from a proximal end portion of the opening window to the proximal end portion of the cover along a direction of the insertion axis passing through a side of the through-hole and torn apart by force from an outside to enable the cover to be removed from the distal end member.

DETAILED DESCRIPTION OF THE PREFERRED EMBODIMENTS

Embodiments of the present invention are explained below with reference to the drawings. Note that the drawings are schematic and relations between thicknesses and widths of respective members, ratios of the thicknesses of the respective members, and the like are different from real ones. It goes without saying that portions, relations and ratios of dimensions of which are different from one another, are included among the drawings.

First Embodiment

Figure 1:
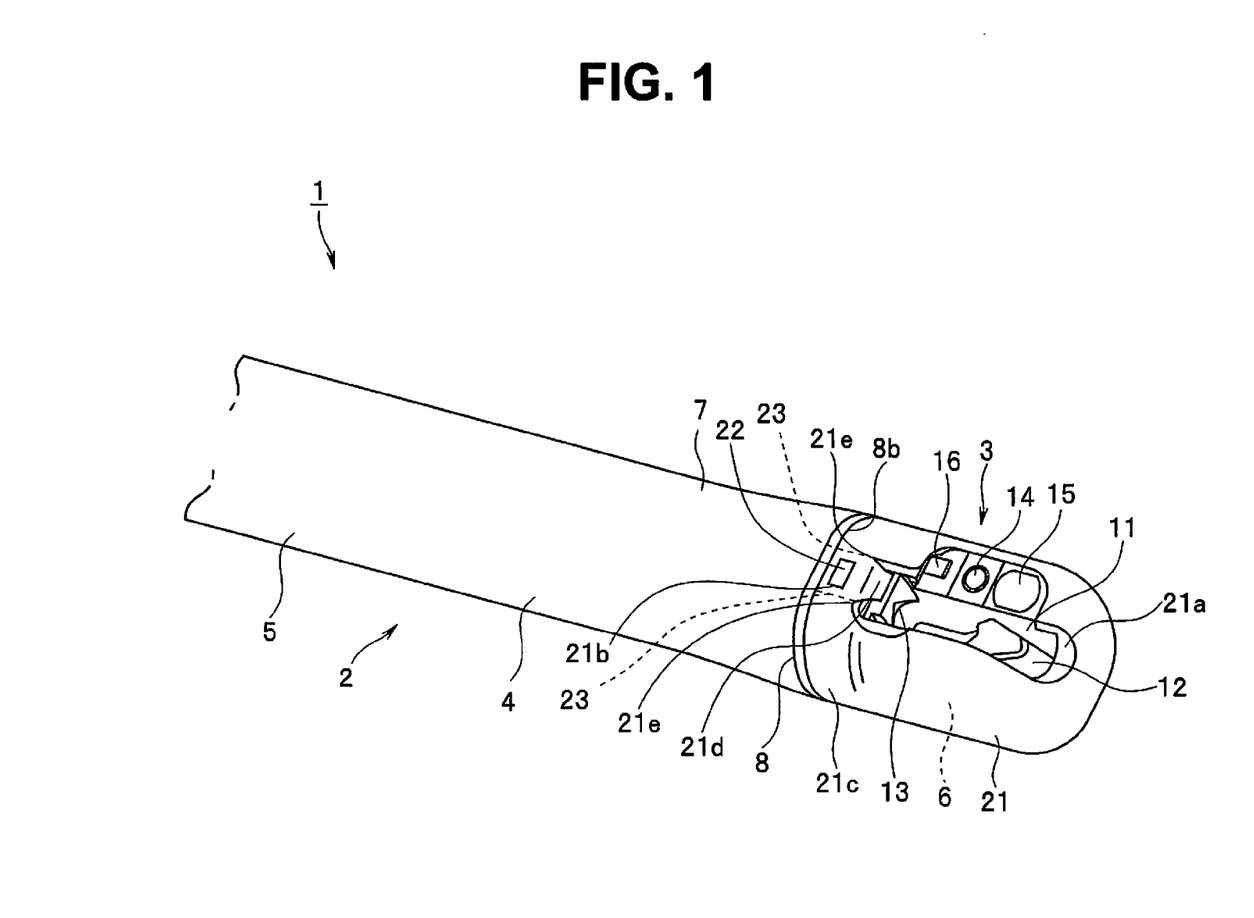
FIG. 1 is a perspective view of a distal end side of an endoscope according to a first embodiment.

A first embodiment of the present invention is shown in FIG. 1 to FIG. 7. In FIG. 1, a main part of an endoscope 1 is shown. The endoscope 1 includes an elongated insertion section 2. An operation section (not shown in the figure), which a surgeon grasps to perform various kinds of operation, is provided on a hand side of the insertion section 2. The insertion section 2 is configured by continuously providing, from a distal end side, a distal end portion 3 of the endoscope, a bending section 4 bendable up and down and to left and right by concatenating a not-shown plurality of bending pieces, and a flexible tube section 5. Note that, in the figure, a side-view type endoscope is shown as the endoscope 1.

Figure 2:
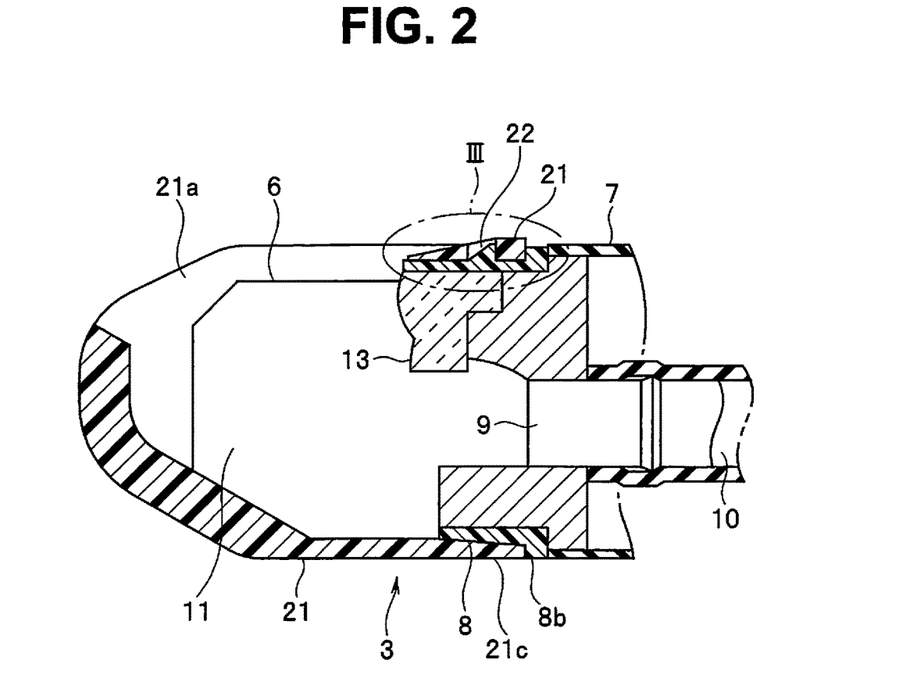
FIG. 2 is a sectional side view of a distal end portion of the endoscope according to the first embodiment.
Figure 4:
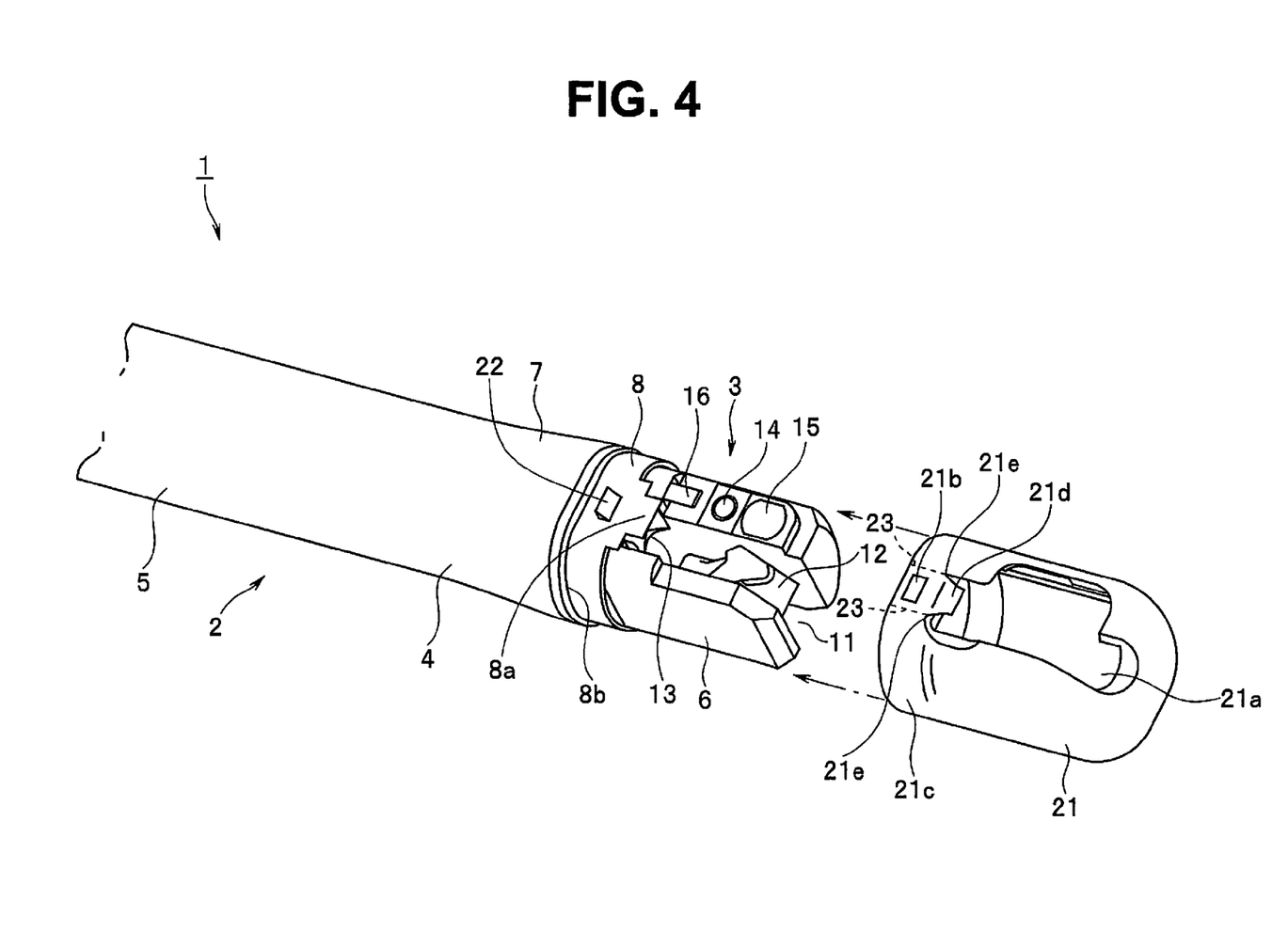
FIG. 4 is a perspective view of a state in which a cover is attached to the distal end portion of the endoscope according to the first embodiment.

As shown in FIG. 2 and FIG. 4, the distal end portion 3 includes a distal end member 6 formed of a metal material. A bending section 4 is concatenated at a proximal end of the distal end member 6. Outer surfaces of the bending section 4 and the flexible tube section 5 are coated with a bending rubber 7 having electric insulation. A front end side of the bending rubber 7 is superimposed on a proximal end portion of the distal end member 6. Further, an insulating ring 8 functioning as an electric insulating member annularly provided around an insertion axis is fit and fixed to a base of the distal end member 6. A rear end of the insulating ring 8 is set in contact with a front end of the bending rubber 7. The insulating ring 8 is a molded product made of resin or ceramic. A base exterior of the distal end member 6 is electrically insulated by the insulating ring 8 and the bending rubber 7. A color different from a color of a cover 21 explained below is kneaded in or surface-painted on the insulating ring 8.

An introducing guide path 9 for guiding a treatment instrument and the like represented by a high-frequency treatment instrument to the distal end side is formed in the distal end member 6. The introducing guide path 9 is formed continuously to an opening end of a forceps channel 10 disposed in the insertion section 2 of the endoscope 1. On the other hand, a housing chamber 11 is provided on the distal end side of the introducing guide path 9. A forceps raising base 12 is disposed in the housing chamber 11. A treatment instrument introduced through the forceps channel 10 or a treatment instrument such as a guide catheter can be raised by a desired angle by the forceps raising base 12. Further, a block member 13 formed of an insulative material that avoids contact with the distal end member 6 when the treatment instrument is bent by the forceps raising base 12 is fixed to a base of the housing chamber 11.

Further, as shown in FIG. 4, an observation window for side view (hereinafter simply referred to as "observation window") 14 and an illumination window 15 that radiates illumination light on an observation visual field are disposed on an upper surface one side on the distal end side of the distal end member 6 from the base side along an axial direction. An air/water feeding nozzle 16 for cleaning the observation window 14 with air/water feeding or the like is disposed on the base side.

A cover 21 is attached to the distal end member 6. The cover 21 is a single use type. As explained below, the cover 21 is discarded when a used endoscope 1 is cleaned and disinfected. The cover 21 has both of flexibility and electric insulation. The cover 21 is formed using, for example, synthetic resin represented by low-density polyethylene (LDPE) having flexibility, elastomer, or a rubber material. Therefore, the distal end member 6 is electrically insulated from a surface of the distal end portion 3 by the cover 21.

The cover 21 is formed in a cap shape including an opening window 21a that exposes the observation window 14, the illumination window 15, the forceps raising base 12, and the like as predetermined. Further, an inner shape of the cover 21 is formed in a shape substantially conforming to an outer shape of the distal end member 6. When the cover 21 is attached to the distal end member 6, the inner shape slides on the outer shape of the distal end member 6 to be guided.

Figure 5:
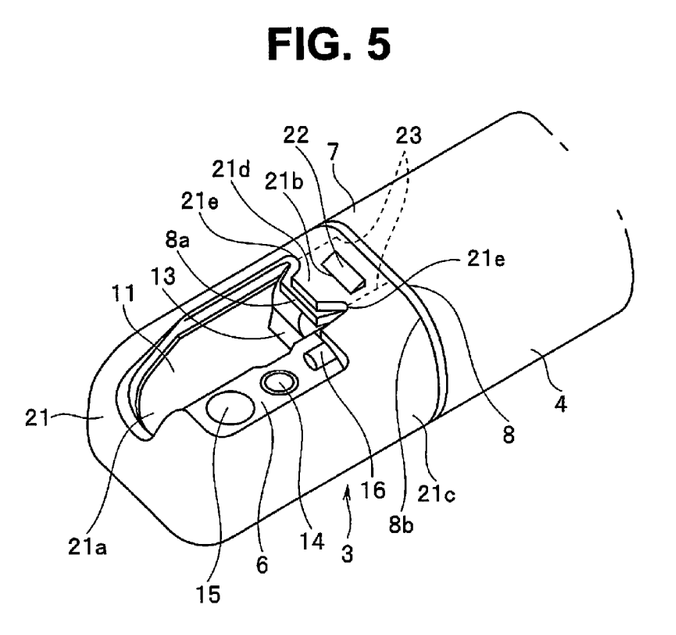
FIG. 5 is a main part perspective view of the distal end portion of the endoscope according to the first embodiment.
Figure 6:
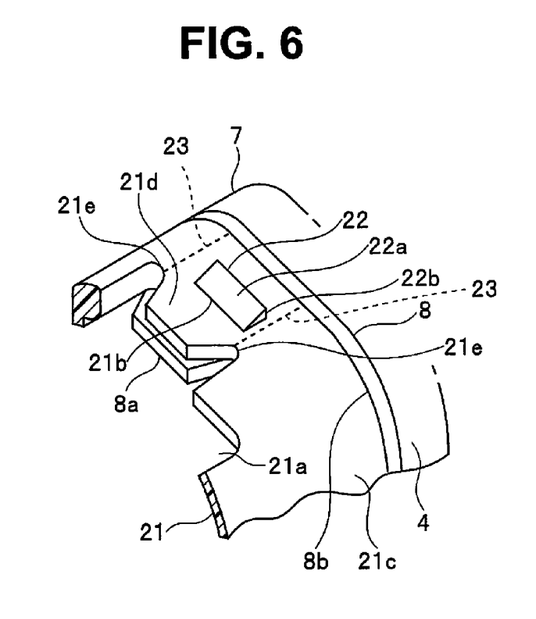
FIG. 6 is a VI part enlarged view of FIG. 5 according to the first embodiment.

As shown in FIG. 2, a projecting section 22 is integrally provided in the insulating ring 8 fit and fixed to the distal end member 6. On the other hand, a through-hole 21b engaging with the projecting section 22 is provided in the cover 21. As shown in FIG. 4 to FIG. 6, the projecting section 22 is provided substantially in a center in a width direction of an upper surface of the distal end portion 3 to project in a direction crossing the insertion axis, that is, upward in the figure. Further, a ring-side tongue piece section 8a is formed in a front of the projecting section 22 in the insulating ring 8. The insulating ring 8 is formed in a tapered shape expanding from the distal end side toward a proximal end side. A stopper section 8b, with which an opening end of the cover 21 comes into contact to be positioned, is formed on a proximal end portion of the insulating ring 8.

Figure 3:
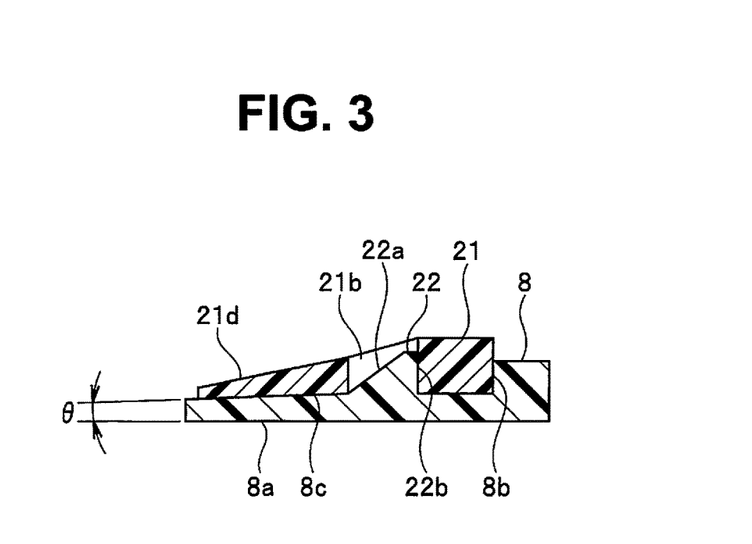
FIG. 3 is a III part enlarged view of FIG. 2 according to the first embodiment.

As shown in FIG. 3, an upper surface of the ring-side tongue piece section 8a is formed as an inclined surface 8c having a predetermined angle θ, an outer shape of which increases from the distal end side toward a proximal end direction. The projecting section 22 is formed halfway on the inclined surface 8c. An outer shape surface 22a directed forward is formed as a tapered surface increasing in an outer shape from the distal end side toward the proximal end side. An end face 22b on the proximal end side is erected in an outer diameter direction of the insulating ring 8. An outer shape of the insulating ring 8, on the proximal end side with respect to the projecting section 22, is set larger than an inner shape of a proximal end portion 21c of the cover 21 explained below to a degree in which the cover 21 is elastically deformed and adheres to the insulating ring 8.

On the other hand, the inner shape of the proximal end portion 21c, in which the through-hole 21b of the cover 21 is drilled, is set small to a degree in which the inner shape of the proximal end portion 21c comes into close contact to the outer shape of the insulating ring 8. Therefore, when the cover 21 is attached to the insulating ring 8, the proximal end portion 21c is closely attached to the insulating ring 8. A cover-side tongue piece section 21d is formed in a front of the through-hole 21b of the cover 21. When the cover 21 is attached to the distal end member 6, the cover-side tongue piece section 21d is disposed on the upper surface of the ring-side tongue piece section 8a. The cover-side tongue piece section 21d is formed in a size smaller than the ring-side tongue piece section 8a. Concave sections 21e turned backward are formed in both side bases of the cover-side tongue piece section 21d.

Further, to-be-torn-apart sections 23 are formed near the through-hole 21b and on width direction both sides. The to-be-torn-apart sections 23 are parts serving as notches in pinching the cover-side tongue piece section 21d with fingers and tearing off the proximal end direction from the cover-side tongue piece section 21d in a state in which the cover 21 is attached to the distal end member 6. As a form of forming the notches, various forms are conceivable.

For example, thin portions extending along the insertion axis are continuously or discontinuously formed to form the to-be-torn-apart sections 23. Alternatively, the to-be-torn-apart sections 23 are formed by linear perforations in positions apart from an outer edge of the through-hole 21b by a predetermined distance. Note that the form of forming the to-be-torn-apart sections 23 may be forms other than the forms explained above.

Action in the present embodiment by such a configuration is explained. When the cover 21 of the single use type is attached to the endoscope 1 cleaned and disinfected as predetermined, first, as shown in FIG. 4, an opening end of the proximal end portion 21c of the cover 21 is inserted along the distal end member 6 from a front surface side of the distal end member 6.

The proximal end portion 21c of the cover 21 is attached to the insulating ring 8 concatenated at a rear end of the distal end member 6. As shown in FIG. 2, an outer circumference of the insulating ring 8 is formed in a tapered shape expanding from the distal end side toward the proximal end side. An inner circumferential surface of the proximal end portion 21c of the cover 21 is guided by an outer circumferential surface of the insulating ring 8 and smoothly attached.

In the projecting section 22 formed substantially in a center in the width direction on the proximal end side of the insulating ring 8, the inclined surface 8c having a predetermined angle θ is formed. Therefore, an inner surface of the proximal end portion 21c of the cover 21 corresponding to the inclined surface 8c is also smoothly moved. When the opening end of the cover 21 reaches the outer shape surface 22a of the projecting section 22, the opening end of the cover 21 is elastically deformed and climbs over the outer shape surface 22a. The through-hole 21b is engaged with the projecting section 22. An engaged state of the projecting section 22 and the through-hole 21b can be easily visually grasped from an outside. Therefore, an attachment error does not occur. In particular, in the present embodiment, the insulating ring 8, in which the projecting section 22 is integrally formed, is colored differently from a color of the cover 21. Therefore, the projecting section 22 exposed from the through-hole 21b is easily visually recognized from the outside. It is possible to more surely grasp whether the projecting section 22 engages with the through-hole 21b. As a result, handleability is high and it is possible to obtain satisfactory workability. Further, a problem such as positional deviation of the cover 21 during use does not occur.

The end face 22b on the proximal end side of the projecting section 22 is a wall surface erected on the insulating ring 8. Therefore, when the through-hole 21b of the cover 21 engages with the projecting section 22, the cover 21 cannot be detached. Further, as shown in FIG. 2 and FIG. 3, in a state in which the through-hole 21b of the cover 21 is engaged with the projecting section 22, the opening end of the cover 21 is set in contact with the stopper section 8b formed at the proximal end of the insulating ring 8. Therefore, a front-back direction of the cover 21 is positioned and fixed. As a result, when the cover 21 is attached, the cover 21 is positions in the insertion axis direction.

An inner circumference of the proximal end portion 21c of the cover 21 is formed slightly smaller than the outer shape of the insulating ring 8. As shown in FIG. 2 and FIG. 3, in a state in which the proximal end portion 21c of the cover 21 is positioned and fixed to the insulating ring 8, the inner circumference of the proximal end portion 21c is set to be closely attached to the insulating ring 8. Therefore, the proximal end side of the cover 21 does not, so to speak, float from the insulating ring 8. It is possible to surely fix the cover 21.

Since the proximal end portion 21c of the cover 21 is superimposed on the insulating ring 8, even if the through-hole 21b is drilled in the proximal end portion 21c, insulation is sufficiently guaranteed. Therefore, even when a high-frequency treatment instrument is used as a treatment instrument, it is possible to prevent a high-frequency electric current from leaking from the through-hole 21b. Since the inner circumference of the proximal end portion 21c is set to be closely attached to the insulating ring 8, it is possible to more surely prevent the leak of the high-frequency current not only from the through-hole 21b but also from a space between the opening end of the cover 21 and the stopper section 8b of the insulating ring 8.

Further, as shown in FIG. 6, the cover-side tongue piece section 21d formed in the cover 21 is formed in a size smaller than the ring-side tongue piece section 8a and is placed on the ring-side tongue piece section 8a. Therefore, the cover-side tongue piece section 21d is less easily turned up during use. Therefore, a part of the to-be-torn-apart sections 23 is not erroneously torn apart.

Thereafter, when cleaning and disinfection treatment is applied to the used endoscope 1 after the use, an operator grasps the cover-side tongue piece section 21d formed in the cover 21 and turns up the cover-side tongue piece section 21d. Then, in the cover-side tongue piece section 21d, starting from the concave sections 21e formed to turn backward, the to-be-torn-apart sections 23 continuing to the concave sections 21e are gradually torn apart.

Figure 7:
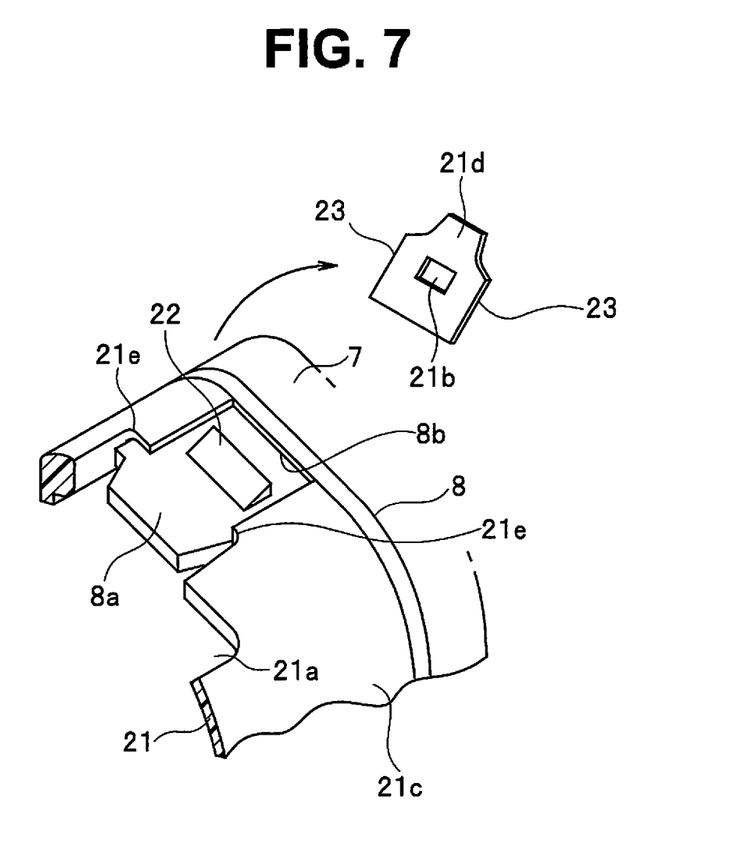
FIG. 7 is a main part perspective view of a state in which to-be-torn-apart sections are torn off from the cover according to the first embodiment.

When the to-be-torn-apart sections 23 are completely torn apart, as shown in FIG. 7, the cover-side tongue piece section 21d is removed from the cover 21 and the through-hole 21b and the projecting section 22 are disengaged. Therefore, the operator can easily remove the cover 21 from the distal end portion 3 and discarded.

Second Embodiment

Figure 8:
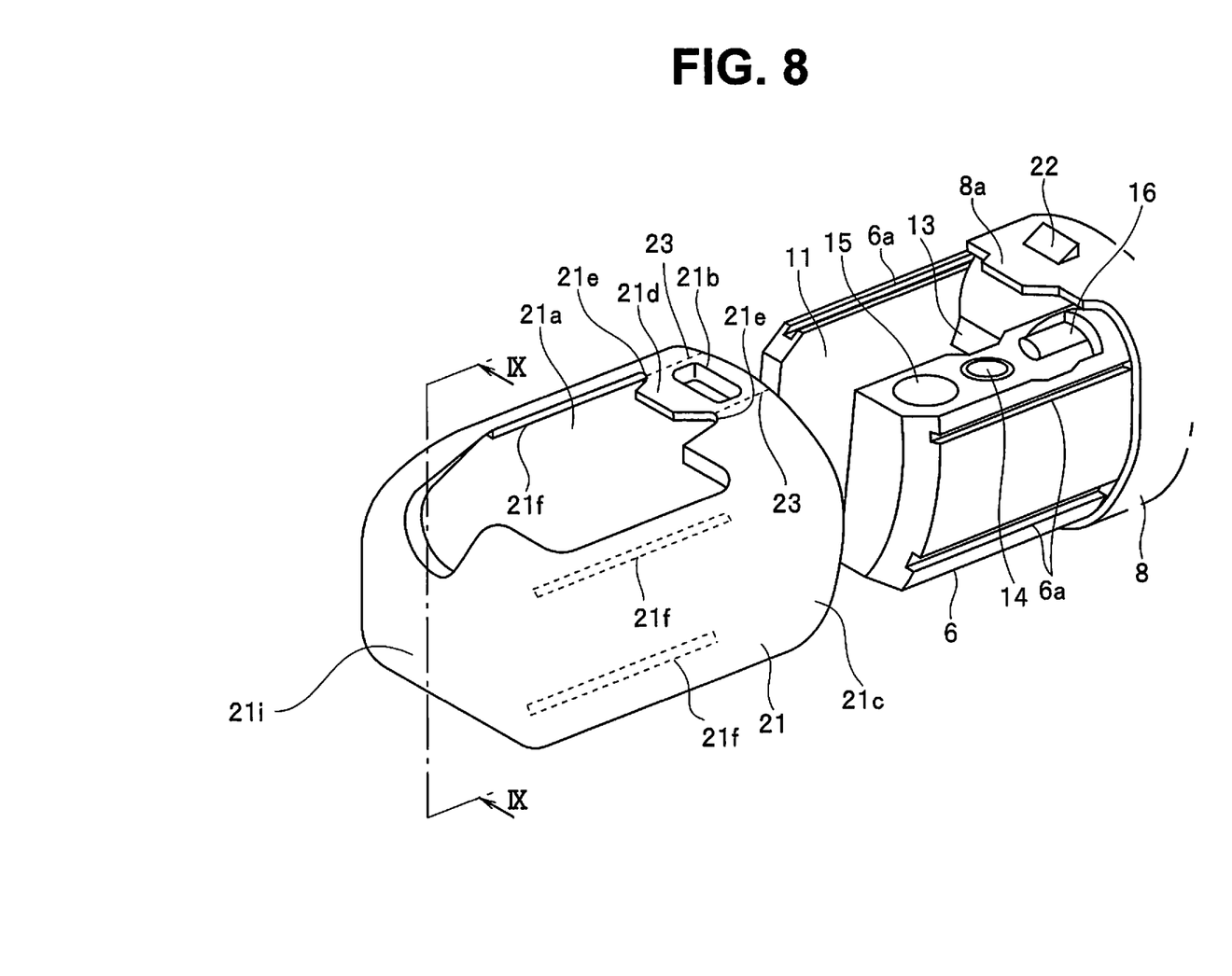
FIG. 8 is a main part perspective view of a state in which a cover is attached to a distal end portion of an endoscope according to a second embodiment of the present invention.
Figure 9:
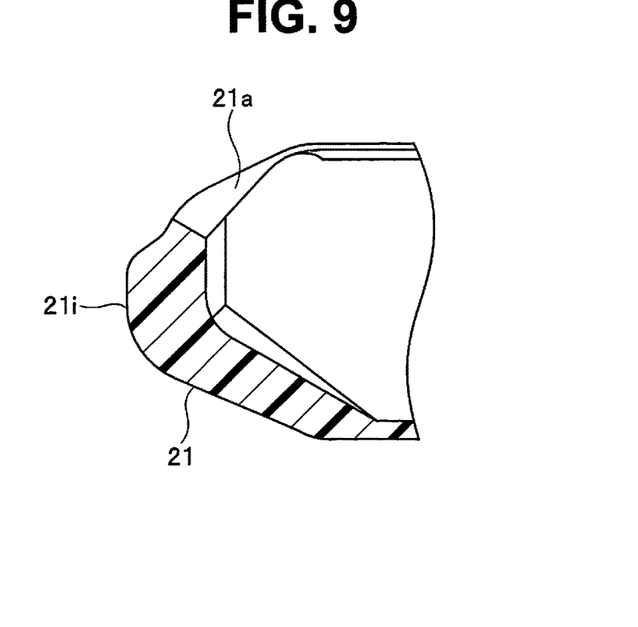
FIG. 9 is a IX-IX sectional view of FIG. 8 according to the second embodiment.

A second embodiment of the present invention is shown in FIG. 8 and FIG. 9. Note that components same as the components in the first embodiment are denoted by the same reference numerals and signs and explanation of the components is omitted.

In the present embodiment, as shown in FIG. 8, long grooves 6a extending along the insertion axis are formed in three places, that is, upper and lower parts of a side surface on one side of the distal end member 6, that is, a side where the observation window 14 and the illumination window 15 are disposed and an upper surface opposed to the side surface across the housing chamber 11. On the other hand, protrusions 21f slidably engaging with the long grooves 6a are formed in positions corresponding to the long grooves 6a on the inner surface of the cover 21 and in a state in which the protrusions 21f project in a direction of the long grooves 6a and extend along the insertion axis direction.

Further, the protrusions 21f and the long grooves 6a are respectively formed further on the distal end side than positions where the projecting section 22 and the through-hole 21b are provided. In this case, at least the protrusions 21f may be formed in a range in which the protrusions 21f do not interfere with a distal end of the insulating ring 8. As shown in FIG. 9, a front end face 21i of the cover 21 is formed with thickness to a degree in which the front end face 21*i* is less easily deformed even if the front end face 21*i* is pressed from the front.

In such a configuration, when the cover 21 is attached to the distal end portion 3, first, the protrusions 21*f* formed on the inner surface of the cover 21 are engaged with the long grooves 6*a* formed in the distal end member 6. Subsequently, the front end face 21*i* of the cover 21 is pressed to move the cover 21 in the insertion axis direction.

Since the cover 21 is moved along the long grooves 6*a*, assemblability is improved. Since the front end face 21*i* of the cover 21 is formed with the thickness in which the front end face 21*i* is less easily deformed even if the front end face 21*i* is pressed, the operator can assemble the cover 21 simply by pressing the front end face 21*i* with fingers without grasping the cover 21. Therefore, in addition to the effects in the first embodiment, it is possible to improve work efficiency.

Note that, in this case, the long grooves 6*a* may be formed in the cover 21 and the protrusions 21*f* may be formed in the distal end member 6. Further, the protrusions 21*f* (or the long grooves 6*a*) formed in the cover 21 may be formed of a hard material and insert-molded in the cover 21. By insert-molding the protrusions 21*f* (or the long grooves 6*a*) in the cover 21, even if the cover 21 is formed of flexible rubber or the like, the protrusions 21*f* (or the long grooves 6*a*) are not elastically deformed. It is possible to obtain satisfactory assemblability.

Third Embodiment

Figure 10:
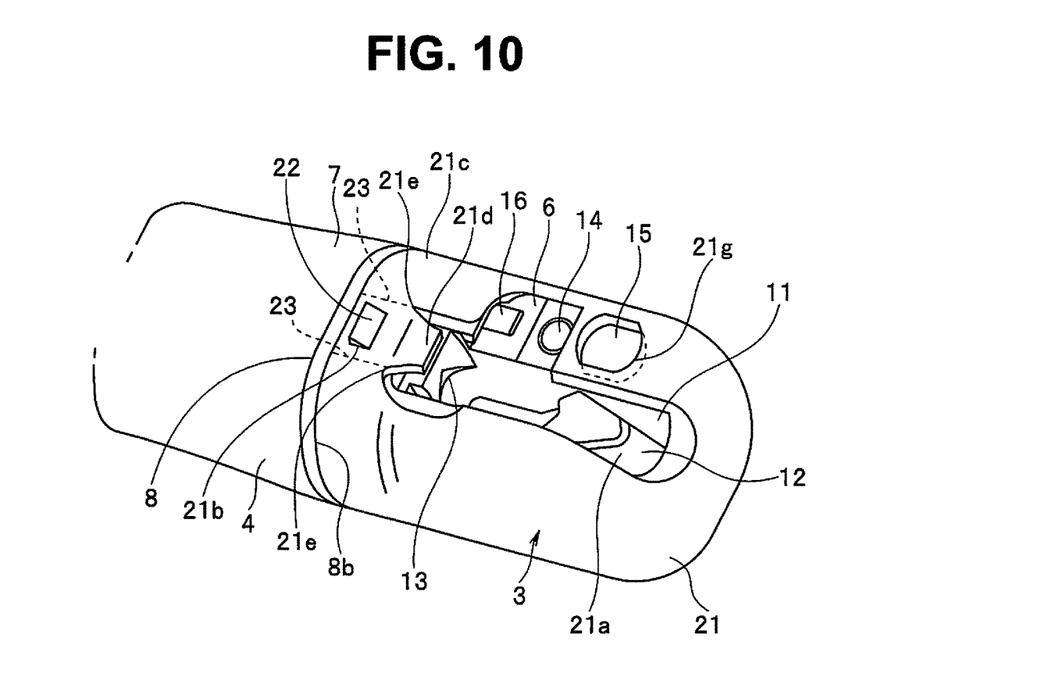
FIG. 10 is a perspective view of a distal end portion of an endoscope according to a third embodiment.

A third embodiment is shown in FIG. 10. In the present embodiment, an illumination hole 21*g* is drilled in a position corresponding to the illumination window 15 of the cover 21. Note that components same as the components in the first embodiment are denoted by the same reference numerals and signs and explanation of the components is omitted.

The illumination hole 21*g* is formed conforming to a contour of the illumination window 15. Consequently, for example, when the cover 21 deviates during use, a part of an outer edge of the illumination hole 21*g* covers the illumination window 15 to reduce a light amount of illumination light. Then, since a light amount of an observation image decreases, it is possible to easily confirm from the decrease in the light amount that the cover 21 deviates.

Fourth Embodiment

Figure 11:
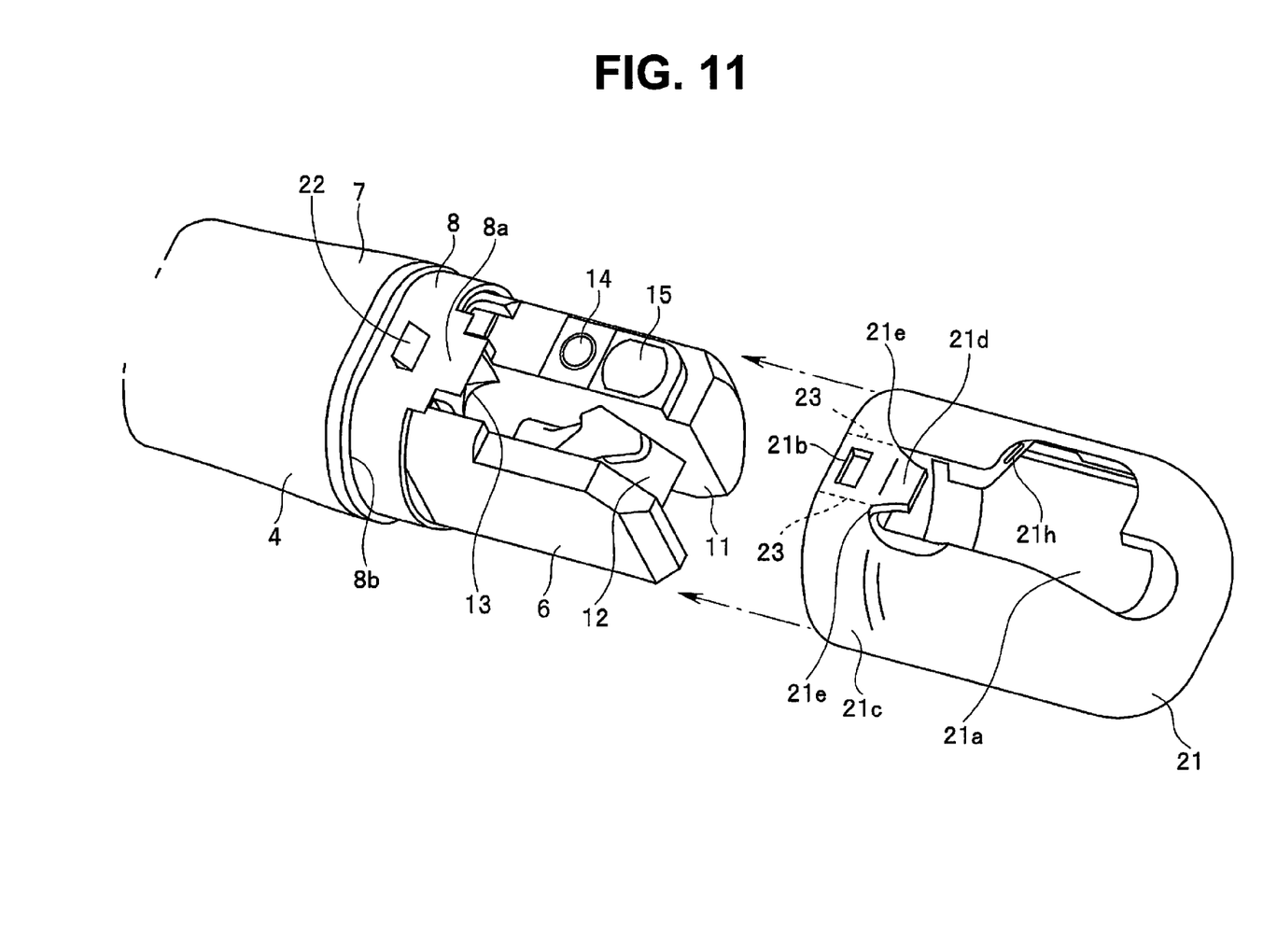
FIG. 11 is a perspective view of a state in which a cover is attached to a distal end portion of an endoscope according to a fourth embodiment.
Figure 12:
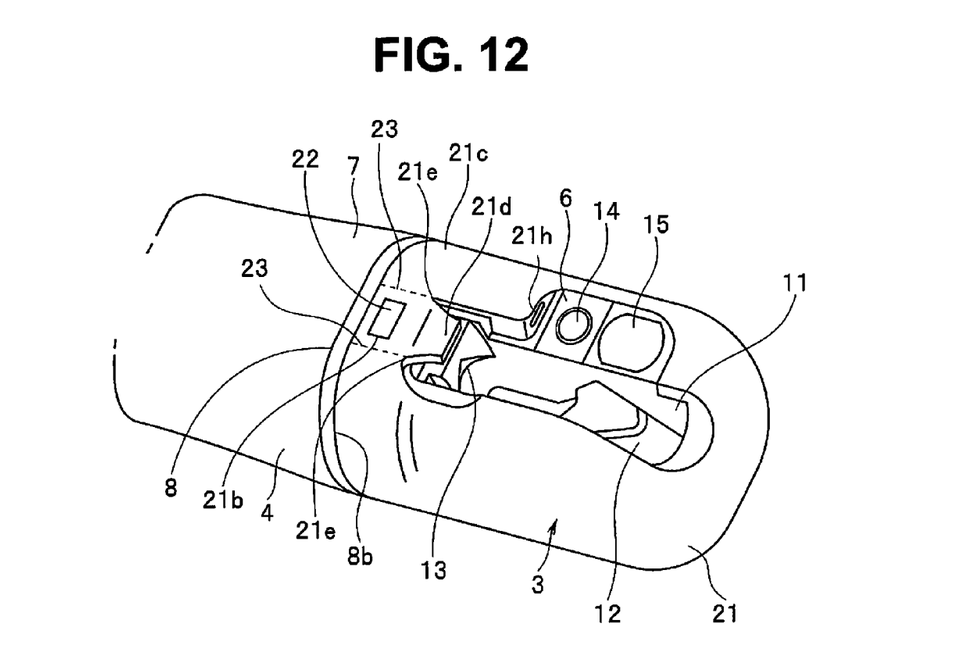
FIG. 12 is a perspective view of a state in which the cover has been attached to the distal end portion of the endoscope according to the fourth embodiment.
Figure 13:
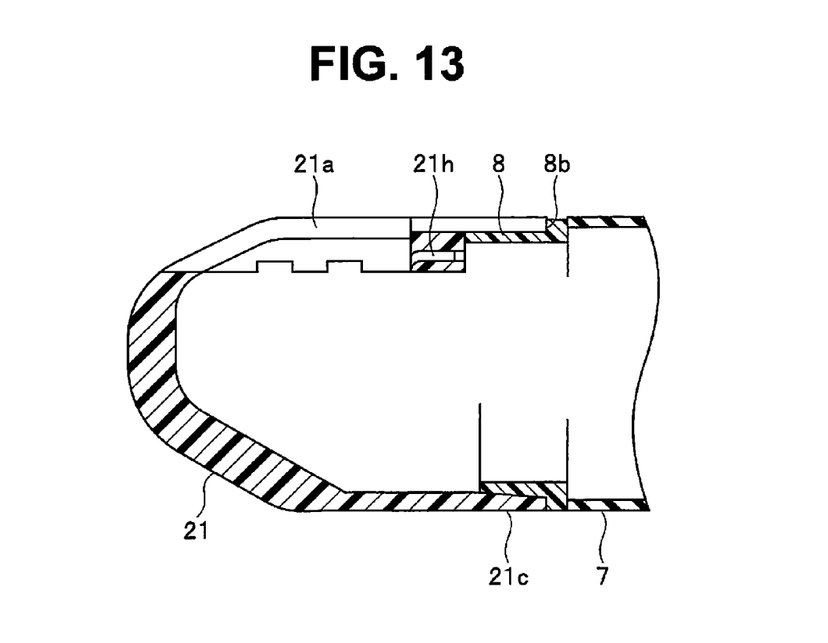
FIG. 13 is a XIII-XIII schematic sectional view of FIG. 12 according to the fourth embodiment.

A fourth embodiment of the present invention is shown in FIG. 11 to FIG. 13. In the present embodiment, an air/water feeding guide passage 21*h* formed in the cover 21 is connected to a distal end of the air/water feeding nozzle 16. A part on the distal end side of the air/water feeding nozzle 16 is formed for single use. Note that components same as the components in the first embodiment are denoted by the same reference numerals and signs and explanation of the components is omitted.

That is, as shown in FIG. 11, the air/water feeding nozzle 16 is formed slightly shorter than usual. Further, as shown in FIG. 13, a distal end portion 16*a* of the air/water feeding nozzle 16 is formed slightly thin to be able to be fit in the air/water feeding guide passage 21*h*.

With such a configuration, when the cover 21 is attached to the distal end member 6 and the proximal end portion 21*c* of the cover 21 is fit in the insulating ring 8, the air/water feeding guide passage 21*h* formed in the cover 21 is connected. The observation window 14 is cleaned by air/water feeding from the air/water feeding guide passage 21*h*.

On the other hand, when the cover 21 is removed from the used endoscope 1 after use, the air/water feeding guide passage 21*h* also comes off the air/water feeding nozzle 16. The distal end portion of the air/water feeding nozzle 16, cleaning and disinfection of which are difficult, are formed for single use by the air/water feeding guide passage 21*h*. Therefore, when the distal end portion 3 is cleaned and disinfected, it is easy to clean and disinfect a vicinity of the distal end portion of the air/water feeding nozzle 16. It is possible to realize improvement of work efficiency.

The present invention is not limited to the embodiments explained above. For example, the endoscope 1 regarded as the subject matter of the present invention is not limited to the side-view type endoscope. The present invention can be applied to any endoscope as long as a distal-end-portion main body is covered with a cover.

What is claimed is:

1. A distal end structure of an endoscope formed to extend along an insertion axis, the distal end structure of the endoscope comprising:
   a distal end member formed of a metal material;
   an insulating member provided around the insertion axis on a proximal end side of the distal end member;
   a cover formed of a flexible insulative material that covers the distal end member;
   a projecting section provided integrally with the insulating member and projecting in a direction crossing the insertion axis;
   an opening window provided in the cover to expose a part of the distal end member;
   a through-hole provided between the opening window in the cover and a proximal end portion of the cover and engaging with the projecting section; and
   a to-be-torn-apart section provided in the cover at a position spaced from each of two sides in a width direction of the through-hole to linearly extend from a proximal end portion of the opening window to the proximal end portion of the cover along a direction of the insertion axis, the to-be-torn-apart section being torn apart from the proximal end portion of the opening window in a direction towards the proximal end portion of the cover, by an applied external force to enable the cover to be removed from the distal end member.

2. The distal end structure of the endoscope according to claim 1, wherein the to-be-torn-apart section is formed by a thin portion extending along the insertion axis.

3. The distal end structure of the endoscope according to claim 2, wherein the thin portion discontinuously continues along the insertion axis.

4. The distal end structure of the endoscope according to claim 1, wherein the to-be-torn-apart section is formed by a perforation extending along the insertion axis.

5. The distal end structure of the endoscope according to claim 1, wherein the distal end member and the cover include a protrusion provided in one of the distal end member and the cover, projecting toward another, and extending along the insertion axis direction, and a long groove provided in the other and extending along the insertion axis direction, the protrusion engaging with the long groove.

6. The distal end structure of the endoscope according to claim 5, wherein the protrusion and the long groove are respectively disposed on a distal end side with respect to positions where the projecting section and the through-hole are provided.

7. The distal end structure of the endoscope according to claim 5, wherein the long groove or the protrusion provided in the cover is formed of a hard material insert-molded into the cover.

8. The distal end structure of the endoscope according to claim 1, wherein an outer shape of the insulating member is set larger than an inner shape of the cover.

9. The distal end structure of the endoscope according to claim 1, wherein an outer surface of the insulating member is formed in a tapered shape expanded from a distal end side toward the proximal end side, and an outer shape of the insulating member is set larger than an outer shape of the cover on the proximal end side with respect to the projecting section.

10. The distal end structure of the endoscope according to claim 1, wherein an outer shape surface of the projecting section is formed as an inclined surface, an outer shape of which increases from a distal end side toward the proximal end side, and an end face on the proximal end side of the projecting section is formed as a surface erected in an outer diameter direction.

11. The distal end structure of the endoscope according to claim 1, wherein a concave section recessed proximally is formed at a distal end edge of the to-be-torn-apart section, and the to-be-torn-apart section and the concave section are disposed on an outer surface of the insulating member.

12. The distal end structure of the endoscope according to claim 1, wherein the to-be-torn-apart section, which is torn apart when the cover is detached, is disposed on the insulating member of a distal end portion in a state in which the cover is attached.

* * * * *